(12) United States Patent
Wang et al.

(10) Patent No.: US 9,388,103 B2
(45) Date of Patent: Jul. 12, 2016

(54) PROCESS FOR PRODUCING PHENOL

(75) Inventors: Kun Wang, Bridgewater, NJ (US);
Roberto Garcia, Easton, PA (US);
Francisco M. Benitez, Cypress, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 116 days.

(21) Appl. No.: 14/343,199

(22) PCT Filed: Aug. 9, 2012

(86) PCT No.: PCT/US2012/050172
§ 371 (c)(1),
(2), (4) Date: Jun. 17, 2014

(87) PCT Pub. No.: WO2013/043271
PCT Pub. Date: Mar. 28, 2013

(65) Prior Publication Data
US 2015/0158801 A1 Jun. 11, 2015

Related U.S. Application Data

(60) Provisional application No. 61/538,332, filed on Sep. 23, 2011.

(30) Foreign Application Priority Data

Nov. 10, 2011 (EP) .................................. 11188530

(51) Int. Cl.
| | | |
|---|---|---|
| *C08G 61/02* | (2006.01) | |
| *C07C 37/08* | (2006.01) | |
| *C07C 45/53* | (2006.01) | |
| *C07C 407/00* | (2006.01) | |
| *C07C 2/74* | (2006.01) | |
| *C07C 39/21* | (2006.01) | |
| *C07C 55/14* | (2006.01) | |
| *C07C 251/44* | (2006.01) | |
| *C07D 223/10* | (2006.01) | |
| *C08G 6/00* | (2006.01) | |
| *C08G 65/38* | (2006.01) | |
| *C08G 69/00* | (2006.01) | |

(52) U.S. Cl.
CPC . *C07C 37/08* (2013.01); *C07C 2/74* (2013.01); *C07C 39/21* (2013.01); *C07C 45/53* (2013.01); *C07C 55/14* (2013.01); *C07C 251/44* (2013.01); *C07C 407/00* (2013.01); *C07D 223/10* (2013.01); *C08G 6/00* (2013.01); *C08G 65/38* (2013.01); *C08G 69/00* (2013.01); *C07C 2101/14* (2013.01); *C07C 2529/70* (2013.01)

(58) Field of Classification Search
CPC ............ C07C 2/66; C07C 2/74; C07C 13/28; C07C 37/08; C07C 39/04; C07C 45/53; C07C 49/403

USPC ........................................................... 528/86
See application file for complete search history.

(56) References Cited

U.S. PATENT DOCUMENTS

| | | |
|---|---|---|
| 3,959,381 A | 5/1976 | Arkell et al. |
| 4,021,490 A | 5/1977 | Hudson |
| 4,439,409 A | 3/1984 | Puppe et al. |
| 4,490,565 A | 12/1984 | Chang et al. |
| 4,490,566 A | 12/1984 | Chang et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,254,751 A | 10/1993 | Zakoshansky |
| 5,362,697 A | 11/1994 | Fung et al. |
| 6,014,018 A | 1/2000 | Wu et al. |
| 6,037,513 A | 3/2000 | Chang et al. |
| 6,077,498 A | 6/2000 | Diaz Cabañas et al. |
| 6,720,462 B2 | 4/2004 | Kuhnle et al. |
| 6,756,030 B1 | 6/2004 | Rohde et al. |

FOREIGN PATENT DOCUMENTS

| | | | |
|---|---|---|---|
| EP | 0 293 032 | 11/1988 | |
| JP | 2007-099746 | * 12/2005 | ............. C07C 27/00 |
| JP | 2007-099745 | 4/2007 | |
| JP | 2007-099746 | 4/2007 | |
| WO | WO 97/17290 | 5/1997 | |
| WO | WO 2009/025939 | 2/2009 | |
| WO | WO 2009/038900 | 3/2009 | |
| WO | WO 2011/001244 | 1/2011 | |
| WO | WO 2012/145031 | 10/2012 | |
| WO | WO 2012/145032 | 10/2012 | |
| WO | WO 2013/052217 | 4/2013 | |

OTHER PUBLICATIONS

Yan et al. Angew. Chem. Int. Ed. 2010, 49, 5549-5553.*
Cole et al., "*Novel Bronsted Acidic Ionic Liquids and Their Use as Dual Solvent-Catalysts*", Journal of the American Chemical Society, American Chemical Society, vol. 124, pp. 5962-5963, May 7, 2002, XP002447834.
Koltunov et al., "*Efficient Cleavage of Cumene Hydroperoxide over HUSY zeolites: The role of Bronsted activity*", Applied Catalysis A: General, vol. 336, pp. 29-34 (2008).
Leng et al., "*Heteropolyanion-Based Ionic Liquids: Reaction-Induced Sefl-Separation Catalysts for Esterification*", Angewandte Chemie (International Edition), 2009, vol. 48, pp. 168-171.

* cited by examiner

*Primary Examiner* — Shane Fang
(74) *Attorney, Agent, or Firm* — Stephen A. Baehl

(57) ABSTRACT

In a process for producing phenol, a feed comprising cyclohexylbenzene hydroperoxide is contacted with a cleavage catalyst comprising an acidic ionic liquid under cleavage conditions effective to cleave at least a portion of said cyclohexylbenzene hydroperoxide and produce a cleavage product stream comprising phenol and cyclohexanone.

11 Claims, No Drawings

PROCESS FOR PRODUCING PHENOL

PRIORITY CLAIM TO RELATED APPLICATIONS

This application is a National Stage Application of International Application No. PCT/US2012/050172 filed Aug. 9, 2012, which claims priority to U.S. Provisional Application Ser. No. 61/538,332 filed Sep. 23, 2011, and European Application No. 11188530.7 filed Nov. 10, 2011, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide generally in the presence of a sulfuric acid catalyst into equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, in which the cyclohexylbenzene is produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide which is then decomposed to the desired phenol and cyclohexanone co-product.

In the cumene-based Hock process, dilute cumene hydroperoxide from the cumene oxidation step is first concentrated to greater than 80% by removing unreacted cumene under vacuum, and the resultant concentrate is then sent to the cleavage reactor. In addition to the hazards associated with handling concentrated hydroperoxide, the cleavage poses safety concerns due to the rapid and highly exothermic nature of the reaction. Further, significant amounts of by-products may be generated from the concentrated oxidation products. In practice, therefore, the concentrated cumene hydroperoxide is often diluted with solvents, such as acetone, in order to better manage the heat of reaction and to control by-product formation. For example, U.S. Pat. No. 5,254,751 discloses a method of producing phenol and acetone by decomposing cumene hydroperoxide in a non-isothermal manner in the presence of excess acetone whereby the molar ratio of acetone to phenol in a decomposition reactor is from about 1.1:1 to 1.5:1.

In producing phenol from cyclohexylbenzene, the problems are different. Firstly, oxidation of cyclohexylbenzene to cyclohexylbenzene hydroperoxide is much more difficult than oxidation of cumene and requires elevated temperatures and the use of a catalyst, such as N-hydroxyphthalimide (NHPI). As a result, the cyclohexylbenzene oxidation effluent is also generally at elevated temperatures so that cooling this stream back to ambient temperature would incur additional operating cost. Also, in view of the high boiling point of cyclohexylbenzene, concentration of the cyclohexylbenzene hydroperoxide by evaporation of the unreacted cyclohexylbenzene is difficult and can lead to unwanted decomposition of the hydroperoxide. Thus, with cyclohexylbenzene hydroperoxide cleavage, the feed contains about 80% hydrocarbon and the products contain only about 20% polar components, which limits sulfuric acid solubility and the cleavage rate. In addition, the cleavage chemistry for cyclohexylbenzene hydroperoxide is much more complicated than that for cumene hydroperoxide, particularly since more routes for by-product formation exist with cyclohexylbenzene hydroperoxide cleavage. Moreover, cyclohexanone is much more prone to acid-catalyzed aldol condensation reactions than acetone so that significant yield loss is possible unless the cyclohexylbenzene hydroperoxide cleavage is closely controlled.

There are other disadvantages of using sulfuric acid for cyclohexylbenzene hydroperoxide cleavage: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

The patent and academic literature is replete with suggestions for replacing sulfuric acid in the cleavage of cumene hydroperoxide. For example, U.S. Pat. No. 4,490,565 discloses that zeolite beta is an effective replacement for sulfuric acid in the cleavage of cumene hydroperoxide and indicates that the yields, conversions and selectivities are generally superior to those produced by the use of the large pore zeolites X and Y. In U.S. Pat. No. 4,490,566, similar improvements over the large pore zeolites X and Y are reported with intermediate pore size zeolites, such as ZSM-5. In contrast, in an article entitled "Efficient Cleavage of Cumene Hydroperoxide Over HUSY Zeolites: The role of Bronsted Activity", *Applied Catalysis A: General*, 336 (2008), pages 29-34, Koltonov et al., report that cumene hydroperoxide readily undergoes decomposition over HUSY zeolites of high (15 to 40) Si/Al ratio with good selectivity to phenol and acetone and with efficiency even comparable to that of sulfuric acid. Despite, or possibly because of these varying recommendations, most commercial processes for the cleavage of cumene hydroperoxide continue to use sulfuric acid as the catalyst.

Less interest has been focused on the cleavage of cyclohexylbenzene hydroperoxide, although International Patent Publication No. WO2011/001244 discloses that cyclohexylbenzene hydroperoxide can be converted to phenol and cyclohexanone in the presence of a variety of homogeneous or heterogeneous acid catalysts selected from protic acids and Lewis acids. Suitable homogeneous catalysts are said to include protic acids selected from sulfuric acid, phosphoric acid, hydrochloric acid, and p-toluenesulfonic acid. Solid Brønsted acids such as Amberlyst and Lewis acids selected from ferric chloride, zinc chloride, boron trifluoride are also disclosed. In addition, suitable heterogeneous acids are said to include zeolite beta, zeolite Y, zeolite X, ZSM-5, ZSM-12, and mordenite.

In addition, Japan Unexamined Patent Publication 2007-099746 discloses that cycloalkyl benzene hydroperoxides can be cleaved with high selectivity to phenol and cycloalkanone in the presence of montmorillonite, silica-alumina, cationic ion exchange resins, and sulfonic acid, perfluorosulfonic acid and heteropolyacids supported on a carrier. Similarly, Japan Unexamined Patent Publication 2007-099745 discloses that cycloalkyl benzene hydroperoxides can be cleaved with high selectivity to phenol and cycloalkanone in the presence of aluminosilicate zeolites having pore diameter of 0.6 nm or greater, such as zeolite Y and zeolite beta.

According to the present invention, it has now been found that acidic ionic liquid catalysts exhibit an advantageous combination of high activity and high selectivity for cleavage of cyclohexylbenzene hydroperoxide to phenol and cyclohexanone. Since these catalyst liquids are generally immiscible with, and heavier than, the cleavage medium, they can be separated from the product simply by settling, without the need for a neutralization step. As a result these acidic ionic liquid catalysts represent an attractive alternative to sulfuric acid for this reaction.

SUMMARY

In one aspect, the invention resides in a process for producing phenol, the process comprising:

(a) contacting a feed comprising cyclohexylbenzene hydroperoxide with a cleavage catalyst comprising an acidic ionic liquid under cleavage conditions effective to cleave at least a portion of said cyclohexylbenzene hydroperoxide and produce a cleavage product stream comprising phenol and cyclohexanone.

Conveniently, said acidic ionic liquid is selected from the following compounds:

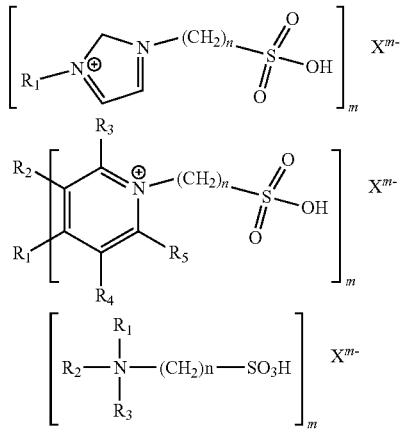

where each of $R_1$, $R_2$, $R_3$, $R_4$, and $R_5$ are the same or different and are independently selected from (a) hydrogen; (b) a hydrocarbyl group having less than 6 carbon atoms; and (c) a hydrocarbyl linker group with less than 6 carbon atoms and a siloxyl group such as —Si(OCH$_3$)$_3$, —Si(OCH$_2$CH$_3$)$_3$, or —Si[OCH(CH$_3$)$_2$]$_3$; n is 2 to 10; m is 1 to 4; and X is an anion with a charge of m.

Conveniently, X is selected from the group comprising $HSO_4^-$, $CF_3SO_3^-$, $(CF_3SO_2)_2N^-$, $BF_4^-$, $PF_6^-$, $AlCl_4^-$, $CuCl_2^-$, $FeCl_4^-$, $SO_4^{2-}$, $PW_{12}O_{40}^{3-}$, $PMo_{12}O_{40}^{3-}$, and $SiW_{12}O_{40}^{4-}$.

In one embodiment, the catalyst further comprises a support. The support can be achieved either via physical adsorption of the acidic ionic liquid on the support, or by anchoring the acidic ionic liquid on the support via chemical bonding or interactions. Such chemical bonding or interaction can be achieved via the siloxyl terminal group on $R_1$, $R_2$, $R_3$, $R_4$, or $R_5$. Conveniently, the support comprises silica, alumina, zirconia, titania, clay, carbon, and mixtures thereof. Alternatively, the support comprises polystyrene.

Conveniently, the cleavage conditions include a temperature of about 10° C. to about 200° C. and a pressure of about 100 kPa to about 1000 kPa.

In one embodiment, at least a portion of the cleavage product stream is cooled and recycled to said contacting step (a).

In a further aspect, the invention resides in a process for producing phenol, the process comprising:

(a) hydroalkylating benzene with hydrogen in the presence of a hydroalkylation catalyst under conditions effective to produce a hydroalkylation reaction product comprising cyclohexylbenzene;

(b) separating cyclohexylbenzene from said hydroalkylation reaction product;

(c) contacting at least a portion of said cyclohexylbenzene from (b) with an oxygen-containing compound in the presence of an oxidation catalyst under oxidation conditions effective to produce an oxidation product comprising cyclohexylbenzene hydroperoxide; and (d) contacting at least a portion of said oxidation product comprising cyclohexylbenzene hydroperoxide with a cleavage catalyst comprising an acidic ionic liquid under cleavage conditions effective to cleave at least a portion of said cyclohexylbenzene hydroperoxide and produce a cleavage product stream comprising phenol and cyclohexanone.

DETAILED DESCRIPTION

Described herein is a process for producing phenol in which a feed comprising cyclohexylbenzene hydroperoxide is contacted with a cleavage catalyst comprising an acidic ionic liquid under cleavage conditions effective to convert at least a portion of the cyclohexylbenzene hydroperoxide into phenol and cyclohexanone. In this respect, the term "ionic liquid" is used herein in its commonly accepted sense to mean a salt that exists in the liquid state at a low temperature, generally below 100° C. It will be understood by one skilled in the art that the definition of "ionic liquid" does not include mineral or protic acids such as sulfuric acid, hydrochloric acid, etc., although such acids may be present in the cleavage catalyst in addition to the ionic liquid. While ordinary liquids such as water and gasoline are predominantly made of electrically neutral molecules, ionic liquids are largely made of ions and short-lived ion pairs.

In one preferred embodiment, the present process forms part of an integrated process for producing phenol from benzene in which the benzene is initially converted to cyclohexylbenzene, conveniently by hydroalkylation. The cyclohexylbenzene is then oxidized to produce cyclohexylbenzene hydroperoxide, which is then subjected to the cleavage operation discussed above. The ensuing description will therefore focus on this integrated process.

Production of Cyclohexylbenzene

In one step of the integrated process starting from benzene, cyclohexylbenzene is produced by reacting the benzene with cyclohexene in the presence of a catalyst having an alkylation function and under conditions to promote the following reaction:

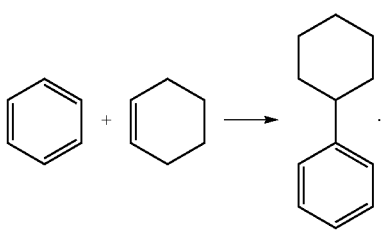

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

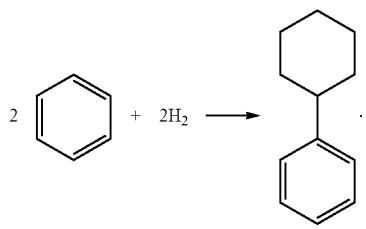 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4:1 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example, at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{1-2}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

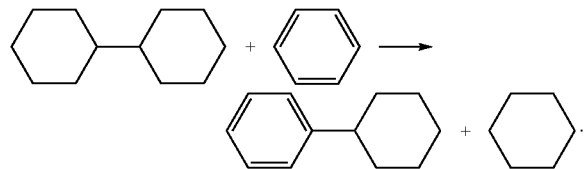

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 1 wt %, such as at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 Å molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

In the present process, the catalyst used in the cleavage reaction comprises an acidic ionic liquid. As discussed above, the term "ionic liquid" means a salt that exists in the liquid state at a low temperature, generally below 100° C. and does not include mineral or protic acids such as sulfuric acid, hydrochloric acid, etc.

In various embodiments, the acidic ionic liquid contains the following structure:

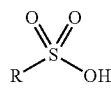

where R is a functional group or side chain that contains one or more carbon atoms and optionally one or more nitrogen atoms.

In various embodiments, suitable acidic ionic liquids include:

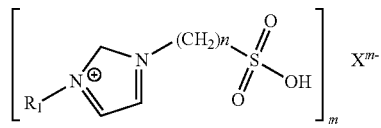

-continued

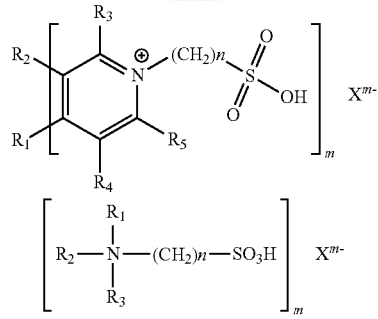

where each of $R_1$, $R_2$, $R_3$, $R_4$, and $R_5$ are the same or different and are independently selected from (a) hydrogen; (b) a hydrocarbyl group having less than 6 carbon atoms; and (c) a hydrocarbyl linker group with less than 6 carbon atoms and a siloxyl group such as $-Si(OCH_3)_3$, $-Si(OCH_2CH_3)_3$, or $-Si[OCH(CH_3)_2]_3$; n is 2 to 10; m is 1 to 4; and X is an anion with a charge of m. As used herein, a "hydrocarbyl group" means a group of hydrogen and carbon atoms that is bonded to the remainder of the molecule via a carbon atom. A "hydrocarbyl linker group" is a hydrocarbyl group having a hydrogen atom replaced with another moiety (i.e., a siloxyl group). Generally, X is selected from the group comprising $HSO_4^-$, $CF_3SO_3^-$, $(CF_3SO_2)_2N^-$, $BF_4^-$, $PF_6^-$, $AlCl_4^-$, $CuCl_2^-$, $FeCl_4^-$, $SO_4^{2-}$, $PW_{12}O_{40}^{3-}$, $PMo_{12}O_{40}^{3-}$, and $SiW_{12}O_{40}^{4-}$. In one embodiment, the acidic ionic liquid is at least partially or substantially immiscible in the cleavage reaction mixture. In one embodiment, the acidic ionic liquid is 1-(4-sulfobutyl)-3-methylimidazolium hydrogen sulfate.

The acidic ionic liquid can be employed as a catalyst in the neat form or can be combined with an inorganic or organic support. The support can be achieved either via physical adsorption of the acidic ionic liquid on the support, or by anchoring the acidic ionic liquid on the support via chemical bonding or interactions. Such chemical bonding or interaction can be achieved via the siloxyl terminal group on $R_1$, $R_2$, $R_3$, $R_4$, or $R_5$. Suitable inorganic supports include silica, alumina, zirconia, titania, clay, carbon and mixtures thereof. Suitable organic supports include polystyrene. Even when used without a support, the acidic ionic liquid is immiscible with, and heavier than, the cleavage reaction medium and will settle from the reaction medium. It can therefore be readily separated by decanting or through fractionation (e.g., distillation). Upstream neutralization of the acidic ionic liquid is not required.

In various embodiments, the cleavage reaction is conducted in the presence of about 10 wppm to about 10,000 wppm, such as about 100 wppm to about 1000 wppm, of the acidic ionic liquid, based upon the total combined weight of the feed and the acidic ionic liquid.

The cleavage reaction medium may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 10° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In one embodiment, the cleavage reactor is a fixed bed reactor. In various embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, which are present in substantially equimolar proportions and can be recovered from the cleavage effluent by any known method.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following Examples.

EXAMPLE 1

Oxidation of Cyclohexylbenzene (CHB)

An amount of 631 g of cyclohexylbenzene (CHB, TCI America, Inc.) was added to a 1-liter four-necked glass flask, to which 0.6702 g of N-hydroxyphthalimide (NHPI, TCI America, Inc.) was added. The flask was then fitted with a reflux condenser, a mechanical stirrer, a gas sparger, and a thermometer. An air flow of 250 cm$^3$/min (cc/min) was bubbled through the liquid via the gas sparger, and the contents of the flask were heated at 110° C. with stirring (560 rpm) for 6 hours. The flask was allowed to cool down to room temperature and the oxidation product recovered. Gas chromatography (GC) analysis indicated the product contains 17.9% cyclohexylbenzene hydroperoxide (CHBHP). The oxidation product also contained about 1060 ppm of NHPI.

EXAMPLE 2

Removal of NHPI from CHB Oxidation Product

An amount of 300 g of the oxidation product from Example 1 was placed in a 500-mL glass flask and mixed with 30 g of anhydrous sodium carbonate (granular form, Aldrich). The mixture was stirred overnight and the solid became brick-red in color. The solid was then removed by filtration and the liquid further filtered through a bed of anhydrous magnesium sulfate. A clear, light-yellow liquid was obtained. GC analysis revealed the product to contain 17.5% CHBHP and <10 ppm NHPI.

EXAMPLE 3

Cleavage of CHBHP Using Sulfuric Acid
(Comparative)

An amount of 30 g mixture of CHBHP/CHB/phenol/cyclohexanone (about 3/81/8/8 wt/wt ratio) and dodecane (internal standard for mass balance calculations) was charged to a 50-mL jacketed glass reactor with a circulating temperature bath. The bath was set to the desired temperature and the reactor contents were allowed to equilibrate. Once the temperature had stabilized, a GC sample was taken for the hot feed. The desired amount of concentrated sulfuric acid (96%, triple-distilled, Aldrich, 500 ppm to liquid feed) was then added via a micro-syringe. After a brief reaction exotherm, as indicated by the temperature rise inside the reactor, a 1-mL aliquot was taken at certain time interval and neutralized with a stoichiometric amount of dihexylamine. The samples generated were analyzed by GC and the results are shown in Table 1.

EXAMPLE 4

Cleavage of CHBHP Using
1-(4-sulfobutyl)-3-methylimidazolium hydrogen
sulfate (Invention)

An amount of 30 grams of mixture containing CHBHP/CHB/phenol/cyclohexanone (about 3/81/8/8 wt. ratio) and dodecane (internal standard for mass balance calculations) was charged to a 50-mL jacketed glass reactor with a circulating temperature bath. The bath was set to 60° C. and the reactor contents were allowed to equilibrate. Once the temperature stabilized (56° C.-57° C.), a GC sample was taken from the hot feed. An amount of 0.19 gram of the acidic ionic liquid 1-(4-sulfobutyl)-3-methylimidazolium hydrogen sulfate (0.1 wt % to liquid feed) was then added to the mixture. A 1-mL aliquot was taken at certain time intervals and analyzed by GC. The results are shown in Table 1.

TABLE 1

| Example | Catalyst & loading | Time (min) | CHBHP conversion (%) | Phenol selectivity (%) | Cyclohexanone selectivity (%) |
|---|---|---|---|---|---|
| 3 | H$_2$SO$_4$ (500 ppm) | 4 | 99 | 95 | 86 |
| 4 | 1-(4-sulfobutyl)-3-methylimidazolium hydrogen sulfate (0.1%) | 30 | 94 | 80 | 88 |

As used herein, "CHBHP conversion" means the amount of cyclohexylbenzene hydroperoxide converted to any product. "Phenol selectivity" is relative to the theoretical phenol yield based upon the amount of cyclohexylbenzene hydroperoxide converted. "Cyclohexanone selectivity" is relative to the theoretical cyclohexanone yield based upon the amount of cyclohexylbenzene hydroperoxide converted. The results in Table 1 show that acidic ionic liquid catalyst exhibits improved selectivity to cyclohexanone as compared with sulfuric acid.

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the scope of the present invention.

The invention claimed is:

1. A process for producing phenol, the process comprising:
    (a) contacting a feed comprising cyclohexylbenzene hydroperoxide with a cleavage catalyst comprising 1-(4-sulfobutyl)-3-methylimidazolium hydrogen sulfate under cleavage conditions effective to cleave at least a portion of said cyclohexylbenzene hydroperoxide and produce a cleavage product stream comprising phenol and cyclohexanone.

2. The process of claim 1, wherein the cyclohexanone selectivity is greater than 86%, based upon the amount of cyclohexylbenzene hydroperoxide converted relative to the theoretical cyclohexanone yield.

3. The process of claim 1, wherein the contacting step (a) is conducted in a continuous loop stirred tank reactor (CSTR).

4. The process of claim 1, wherein the feed comprises 1 wt % to 30 wt % of cyclohexylbenzene hydroperoxide, based upon total weight of the feed.

5. The process of claim 1, wherein the contacting step (a) is conducted in the presence of about 10 wppm to about 10,000 wppm of the acidic ionic liquid, based upon the total combined weight of the feed and the acidic ionic liquid.

6. The process of claim 1, wherein at least a portion of the acidic ionic liquid is present in the cleavage product stream, and the process further comprises:
    (b) separating at least a portion of the acidic ionic liquid from the cleavage product stream.

7. The process of claim 6, wherein the acidic ionic liquid present in the cleavage product stream is not neutralized upstream of the separating step (b).

8. The process of claim 1, wherein said catalyst further comprises a support.

9. The process of claim 8, wherein said support comprises silica, alumina, zirconia, titania, clay, carbon, polystyrene, and mixtures thereof.

10. The process of claim 1, wherein said cleavage conditions include a temperature of about 10° C. to about 200° C. and a pressure of about 100 kPa to about 1000 kPa.

11. The process of claim 1, wherein at least a portion of said a cleavage product stream is cooled and recycled to said contacting step (a).

* * * * *